United States Patent
Cleary et al.

(10) Patent No.: US 11,389,686 B2
(45) Date of Patent: Jul. 19, 2022

(54) ROBOTICALLY ASSISTED ANKLE REHABILITATION SYSTEMS, APPARATUSES, AND METHODS THEREOF

(71) Applicant: CHILDREN'S NATIONAL MEDICAL CENTER, Washington, DC (US)

(72) Inventors: Kevin Cleary, Washington, DC (US); Sarah Evans, Washington, DC (US); Reza Monfaredi, Washington, DC (US); Hadi F. Talari, Washington, DC (US); Catherine Coley, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 439 days.

(21) Appl. No.: 16/339,214

(22) PCT Filed: Oct. 9, 2017

(86) PCT No.: PCT/US2017/055760
§ 371 (c)(1),
(2) Date: Apr. 3, 2019

(87) PCT Pub. No.: WO2018/068037
PCT Pub. Date: Apr. 12, 2018

(65) Prior Publication Data
US 2020/0038703 A1    Feb. 6, 2020

Related U.S. Application Data

(60) Provisional application No. 62/405,584, filed on Oct. 7, 2016.

(51) Int. Cl.
*A63B 21/00* (2006.01)
*A61H 1/00* (2006.01)
(Continued)

(52) U.S. Cl.
CPC ....... *A63B 21/00178* (2013.01); *A61H 1/005* (2013.01); *A61H 1/0266* (2013.01);
(Continued)

(58) Field of Classification Search
CPC .............. A63B 21/00178; A63B 23/08; A63B 24/0062; A63B 24/0075;
(Continued)

(56) References Cited

U.S. PATENT DOCUMENTS

| 4,605,220 A | * | 8/1986 | Troxel | A63B 23/08 |
| | | | | 482/79 |
| 4,826,159 A | * | 5/1989 | Hersey | A63B 26/003 |
| | | | | 482/146 |

(Continued)

FOREIGN PATENT DOCUMENTS

WO    WO 2009/125397 A2    10/2009

OTHER PUBLICATIONS

International Search Report dated Jan. 12, 2018 in PCT/US2017/055760 filed on Oct. 9, 2017.

*Primary Examiner* — Garrett K Atkinson
(74) *Attorney, Agent, or Firm* — Oblon, McClelland, Maier & Neustadt, L.L.P.

(57) ABSTRACT

Systems, apparatuses, and methods for performing robotically assisted physical therapy. The system, apparatus, and method can include a motion platform having three-degrees of freedom to achieve pitch motion, yaw motion, and roll motion; a plurality of motors connected to the motion platform to enable the pitch motion, the yaw motion, and/or the roll motion; at least one sensor configured to collect data relating to position and/or motion of the motion platform; and a motion controller configured to control the motion platform based on the collected data and/or external commands.

18 Claims, 14 Drawing Sheets

(51) Int. Cl.
  *A61H 1/02* (2006.01)
  *A63B 23/08* (2006.01)
  *A63B 24/00* (2006.01)
(52) U.S. Cl.
  CPC .......... *A63B 23/08* (2013.01); *A63B 24/0062* (2013.01); *A63B 24/0075* (2013.01); *A61H 2201/1207* (2013.01); *A61H 2201/1642* (2013.01); *A61H 2201/1659* (2013.01); *A61H 2201/501* (2013.01); *A61H 2201/5007* (2013.01); *A61H 2201/5046* (2013.01); *A61H 2201/5061* (2013.01); *A61H 2201/5097* (2013.01); *A61H 2230/605* (2013.01); *A63B 2024/0093* (2013.01); *A63B 2024/0096* (2013.01); *A63B 2220/30* (2013.01); *A63B 2220/51* (2013.01); *A63B 2220/54* (2013.01); *A63B 2220/803* (2013.01); *A63B 2225/20* (2013.01); *A63B 2230/085* (2013.01)
(58) Field of Classification Search
  CPC .... A63B 2024/0093; A63B 2024/0096; A63B 2220/30; A63B 2220/51; A63B 2220/54; A63B 2220/803; A63B 2225/20; A63B 2230/085; A63B 21/0058; A63B 24/0087; A63B 21/00181; A63B 2230/605; A63B 24/0059; A63B 2024/0015; A63B 2024/0068; A63B 2071/0072; A63B 2071/0081; A63B 2071/063; A63B 2071/068; A63B 2071/0683; A63B 2220/12; A63B 2220/16; A63B 2220/17; A63B 2220/40; A63B 2220/805; A63B 2220/807; A63B 2225/50; A61H 1/005; A61H 1/0266; A61H 2201/1207; A61H 2201/1642; A61H 2201/1659; A61H 2201/5007; A61H 2201/501; A61H 2201/5046; A61H 2201/5061; A61H 2201/5097; A61H 2230/605; A61H 2201/5064; A61H 2201/5071; A61H 2201/5079; A61H 2201/5092; G06F 3/016; G06F 3/0334; G06F 3/038; G06F 3/0346; G16H 20/30
  See application file for complete search history.

(56) References Cited

U.S. PATENT DOCUMENTS

| | | | | |
|---|---|---|---|---|
| 5,168,634 A * | 12/1992 | Misevich | ............. | B23Q 1/5412 600/592 |
| 5,335,674 A * | 8/1994 | Siegler | ................ | A61B 5/103 600/595 |
| 5,518,476 A * | 5/1996 | McLeon | ............... | A63B 23/08 482/79 |
| 5,722,919 A * | 3/1998 | Timmer | ................ | A63B 23/08 482/79 |
| 5,897,464 A * | 4/1999 | Mcleod | ................ | A63B 23/08 601/27 |
| 5,897,474 A * | 4/1999 | Romero | ................ | A63B 22/14 482/79 |
| 5,902,214 A * | 5/1999 | Makikawa | ............ | G16H 20/30 482/52 |
| 5,987,726 A * | 11/1999 | Akeel | ................ | B25J 17/0216 29/709 |
| 6,162,189 A * | 12/2000 | Girone | ................ | A63B 23/08 600/595 |
| 6,872,175 B2 * | 3/2005 | Lin | ...................... | A63B 26/003 482/121 |
| 7,011,612 B2 * | 3/2006 | Repking | ............... | A63B 22/16 482/79 |
| 7,357,766 B2 * | 4/2008 | Langer | .................. | A63B 22/18 482/146 |
| 7,641,591 B2 * | 1/2010 | Takizawa | ........... | A63B 21/4015 482/8 |
| 9,271,895 B2 * | 3/2016 | Mor | ..................... | A63B 22/18 |
| 9,889,058 B2 * | 2/2018 | Horst | ................... | A61H 1/0277 |
| 9,962,574 B2 * | 5/2018 | Sperry | .................. | A63B 22/18 |
| 10,065,068 B1 * | 9/2018 | Wilson | .............. | A63B 21/4034 |
| 10,080,915 B2 * | 9/2018 | Waldner | ............. | A63B 21/023 |
| 10,475,690 B2 * | 11/2019 | Ng | ...................... | H01L 21/6838 |
| 10,675,202 B2 * | 6/2020 | Kim | ..................... | A61H 1/0266 |
| 10,850,389 B2 * | 12/2020 | Nalam | .................. | B25J 19/02 |
| 10,967,220 B2 * | 4/2021 | Gouzenko | .............. | A63G 23/00 |
| 10,967,237 B2 * | 4/2021 | Gouzenko | .............. | A63B 23/08 |
| 2004/0023766 A1 * | 2/2004 | Slone | .................. | A63B 26/003 482/146 |
| 2004/0034282 A1 | 2/2004 | Quaid, III | | |
| 2010/0035734 A1 * | 2/2010 | DiGiovanni | ......... | A63B 23/085 482/79 |
| 2011/0256983 A1 * | 10/2011 | Malack | ............... | A63B 21/4015 482/4 |
| 2013/0116726 A1 * | 5/2013 | Mor | ...................... | A43B 7/147 606/204 |
| 2015/0011362 A1 | 1/2015 | Oh et al. | | |
| 2015/0328497 A1 * | 11/2015 | Doucot | ............... | A63B 24/0062 482/146 |
| 2016/0067550 A1 * | 3/2016 | Breach | .................. | A43B 3/246 36/103 |
| 2017/0128816 A1 * | 5/2017 | DeMarch | ............. | G09B 19/003 |

* cited by examiner

ROBOTICALLY ASSISTED ANKLE REHABILITATION SYSTEMS, APPARATUSES, AND METHODS THEREOF

CROSS-REFERENCE TO RELATED APPLICATIONS

The present application claims priority to Provisional App. No. 62/405,584 filed Oct. 7, 2016, the entire substance of which is incorporated herein by reference.

FIELD OF THE DISCLOSURE

This disclosure relates generally to improvements to a robotic platform. More particularly, improvements related to robotically assisted ankle physical therapy for patients with cerebral palsy or other neuromuscular disorders.

SUMMARY

According to one or more embodiments, a robotic platform system can comprise: a motion platform having three-degrees of freedom to achieve a pitch motion, a yaw motion and a roll motion; a plurality of motors connected to the motion platform to enable the pitch motion, the yaw motion and the roll motion of the motion platform; at least one sensor to collect data related to a motion including a range of motion, a number of repetitions, a speed, a force, or a torque; and a motion controller configured to receive the collected data from the at least one sensor, analyze the data to determine motion patterns, improvement over past performance and recommend new motion patterns to improve future performance.

In one or more embodiments, a method for operating a robotic platform can comprise: receiving data from at least one sensor of the robotic platform; and analyzing the data to determine motion patterns, improvement over past performance and recommend new motion patterns to improve future performance.

In one or more embodiments, a non-transitory computer-readable medium storing a program which when executed by a computer, causes the computer to perform a method for controlling a robotic platform can be provided. The method can comprise: receiving data from at least one sensor of the robotic platform; and analyzing the data to determine motion patterns, improvement over past performance and recommend new motion patterns to improve future performance.

According to one or more embodiments of the disclosed subject matter, a robotic platform system can be provided. The system can comprise: a motion platform having three-degrees of freedom to achieve a pitch motion, a yaw motion and a roll motion; a plurality of motors connected to the motion platform to enable the pitch motion, the yaw motion and the roll motion of the motion platform; at least one sensor to collect data related to a motion including a range of motion, a number of repetitions, a speed, a force, or a torque; and a motion controller configured to receive the collected data from the at least one sensor, analyze the data to determine motion patterns, improvement over past performance and recommend new motion patterns to improve future performance, adjust a resistance level by adjusting the force or torque of at least one of the plurality of motors based on the analyzed data to customize motion patterns according to a performance feedback of a user, capture motions of the motion platform and transmit the motions to a game controller to achieve gaming tasks related to the motions, detect fatigue in a foot of the user based on the sensor data and provide power assistance to complete a motion, and control the movement of the plurality of motors.

One or more embodiments may involve a method of operating a robotic platform. The method can comprise: receiving data from at least one sensor of the robotic platform; analyzing the data to determine motion patterns, improvement over past performance and recommend new motion patterns to improve future performance; adjusting, via a network, a resistance level by adjusting a force or a torque of at least one of a plurality of motors of the robotic platform based on the analyzed data to customize motion patterns according to a performance feedback of a user; capturing motions of a motion platform of the robotic platform and transmitting the motions to a game controller to achieve gaming tasks related to the motions; detecting fatigue in a foot of the user based on the sensor data and providing a power assistance to complete a motion; and controlling the movement of the plurality of motors.

One or more embodiments may involve a non-transitory computer-readable medium storing a program which when executed by a computer, causes the computer to perform a method for controlling a robotic platform. The method can comprise: receiving data from at least one sensor of the robotic platform; analyzing the data to determine motion patterns, improvement over past performance and recommend new motion patterns to improve future performance; adjusting a resistance level by adjusting a force or a torque of at least one of a plurality of motors of the robotic platform based on the analyzed data to customize motion patterns according to a performance feedback of a user; and capturing motions of a motion platform of the robotic platform and transmitting the motions to a game controller to achieve gaming tasks related to the motions.

Embodiments of the disclosed subject matter can also involve methods, including methods of providing the treatments, systems, and/or apparatuses according to the present disclosure, methods of using or applying the treatments, systems, and/or apparatuses according to the present disclosure, and methods of treatment using systems and/or apparatuses according to the present disclosure.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION

Figure 1:
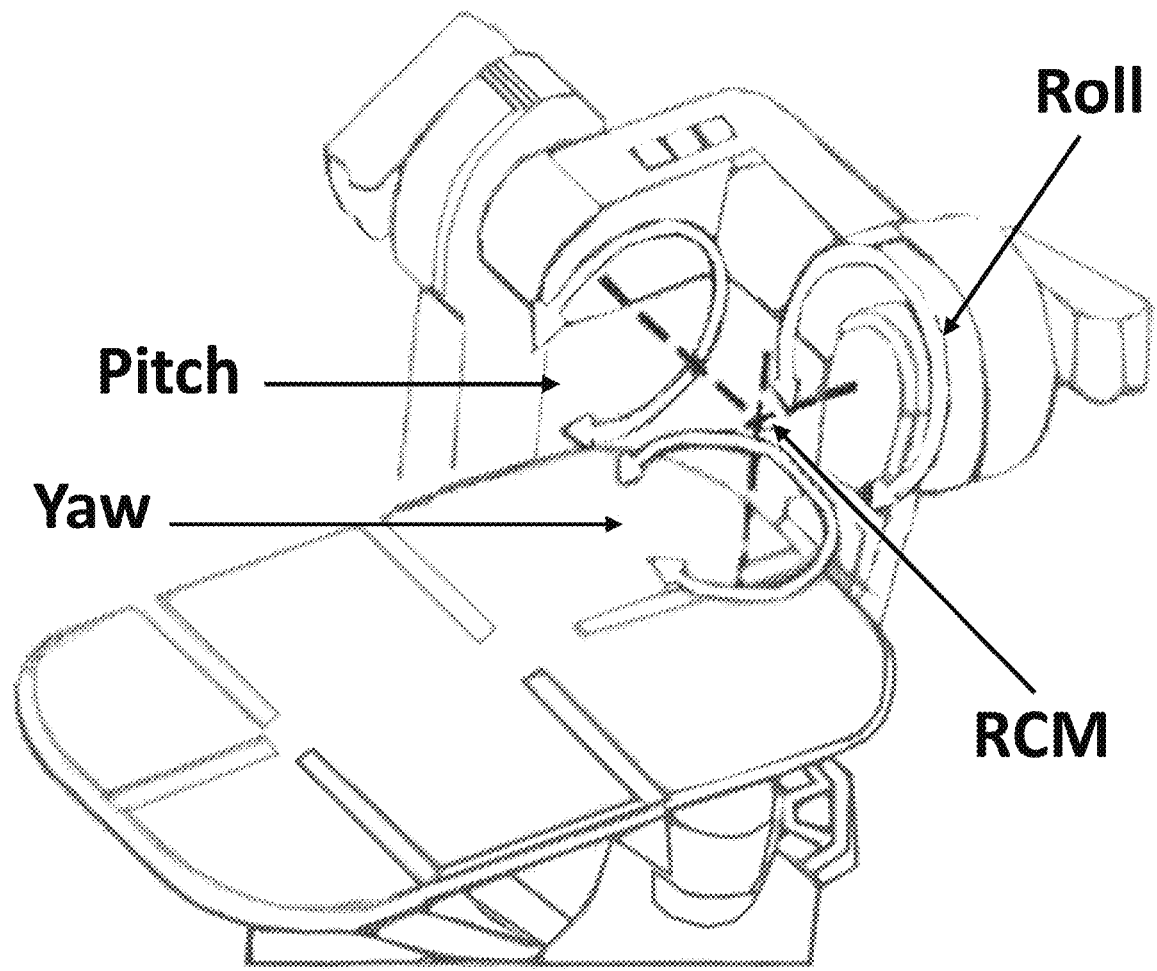
FIG. 1 is a perspective illustration of a robotic system according to one or more embodiments of the present disclosure.
Figure 2:
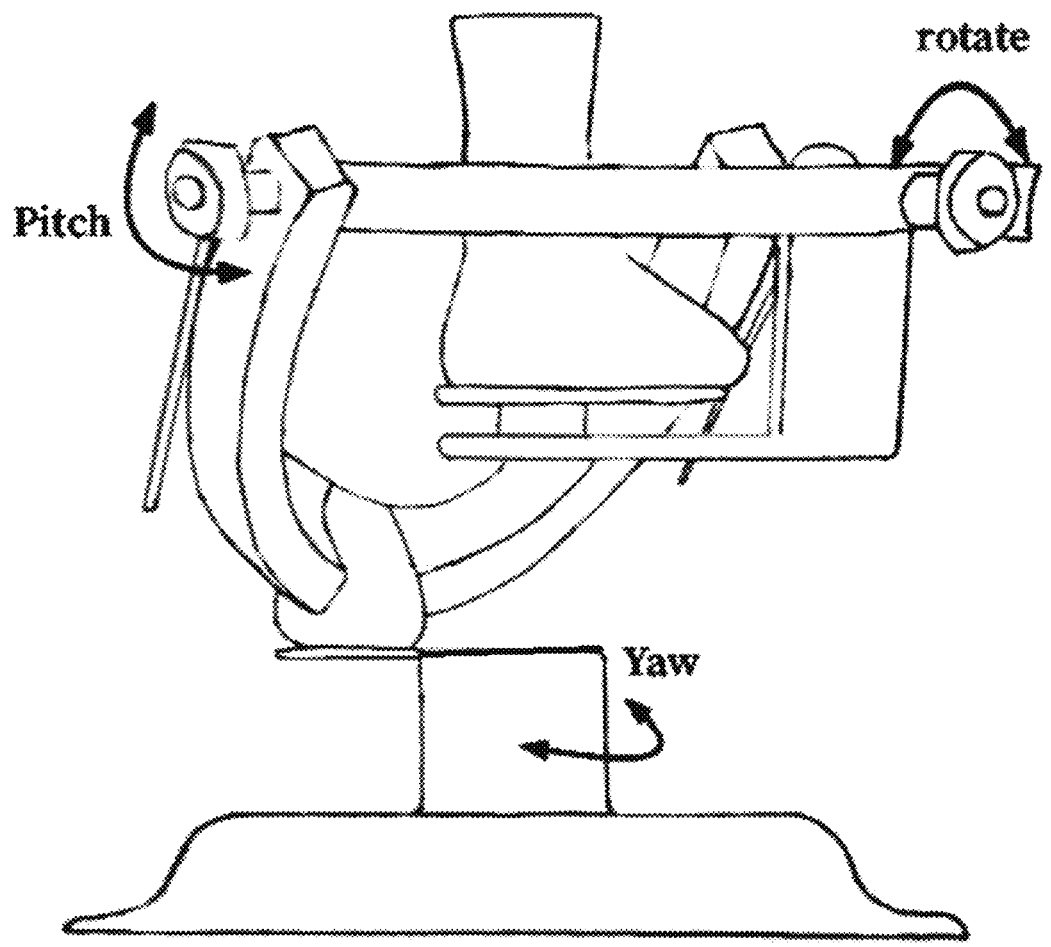
FIG. 2 is a perspective illustration of a robotic platform according to an exemplary embodiment of the present disclosure.
Figure 3:
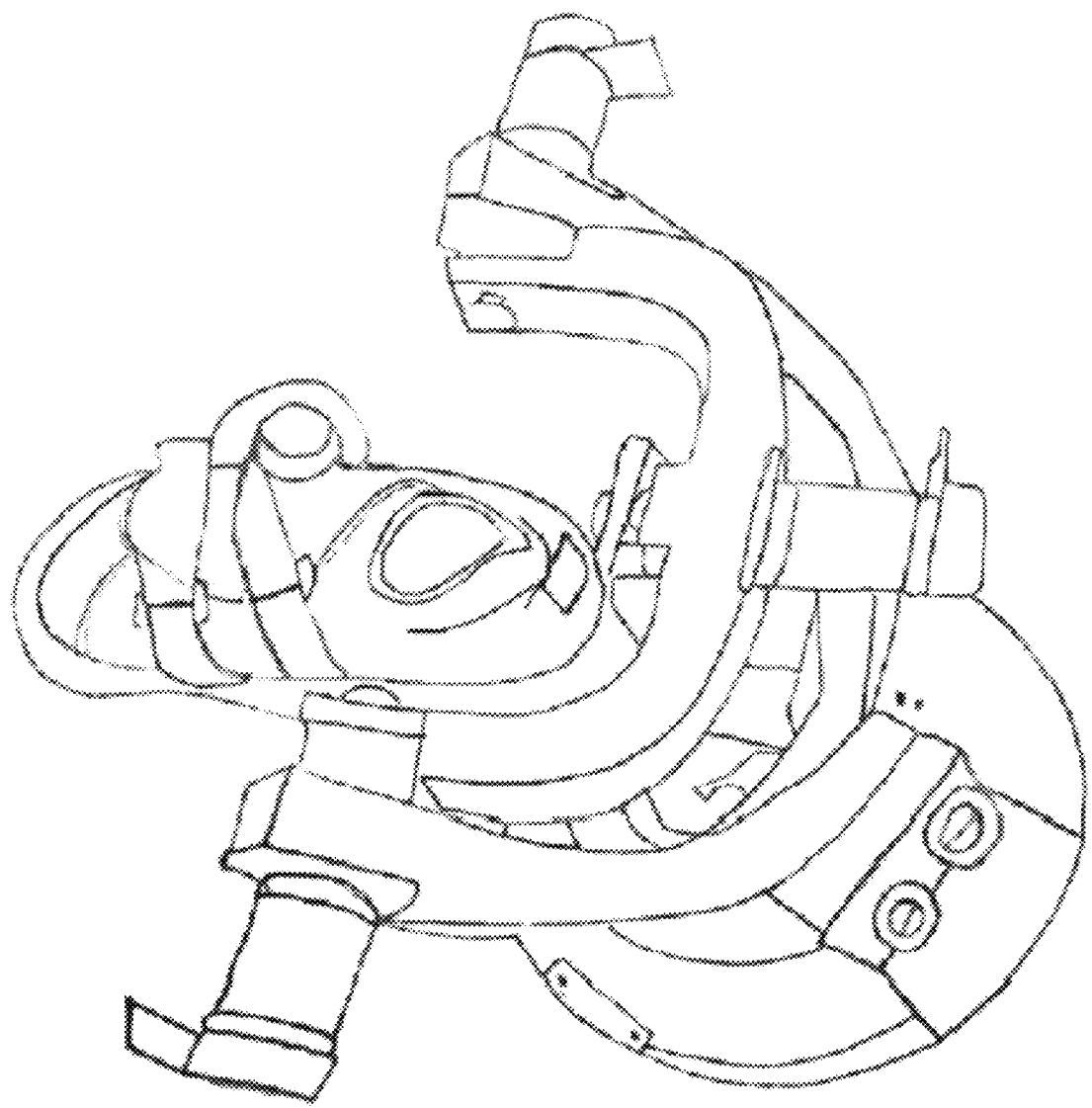
FIG. 3 is a top view of the robotic platform according to an exemplary embodiment of the present disclosure.
Figure 4:
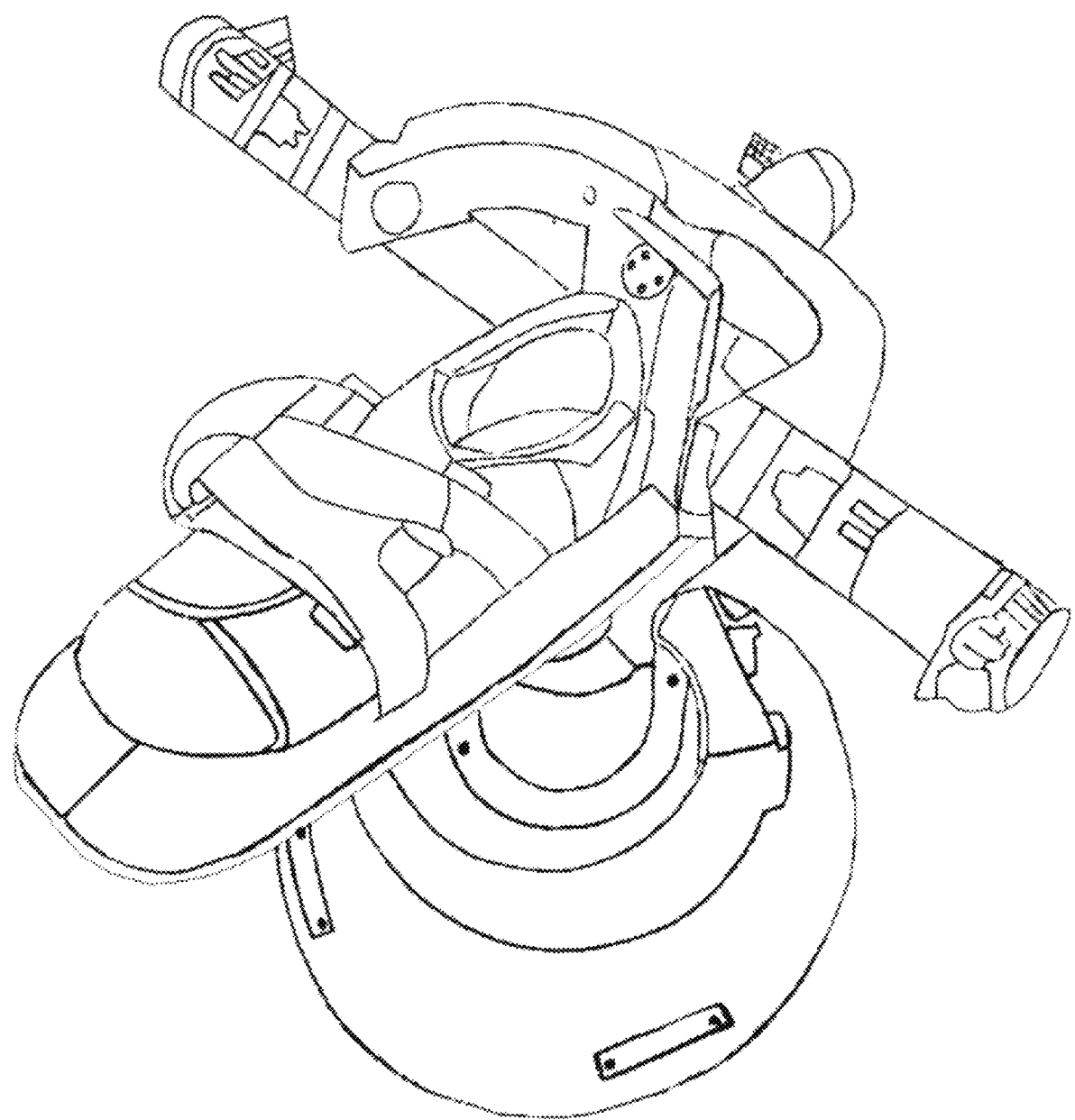
FIG. 4 is a front view of the robotic platform according to an exemplary embodiment of the present disclosure.
Figure 5:
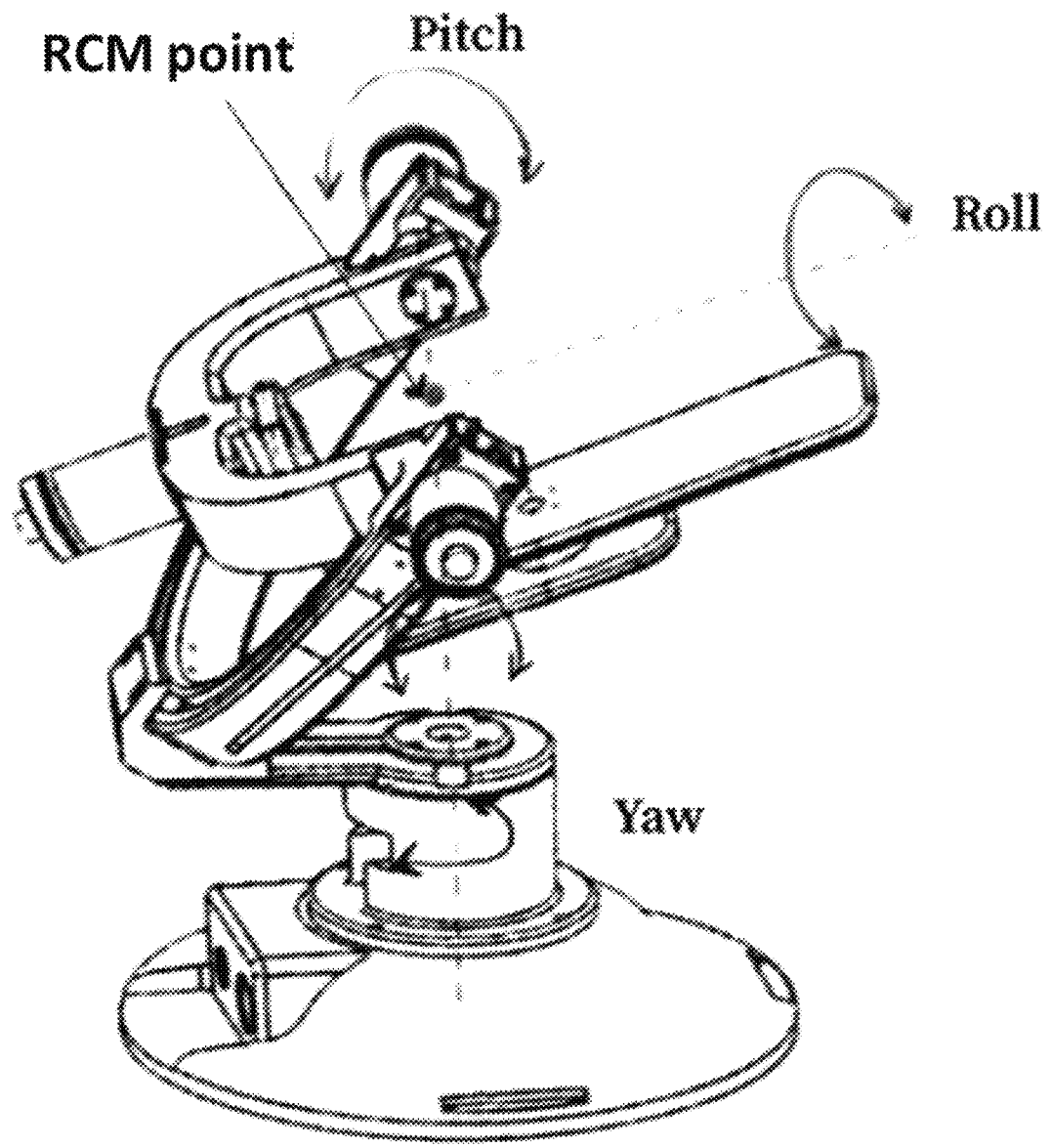
FIG. 5 is a perspective illustration of a robotic platform showing the different motions according to an exemplary embodiment of the present disclosure.
Figure 6:
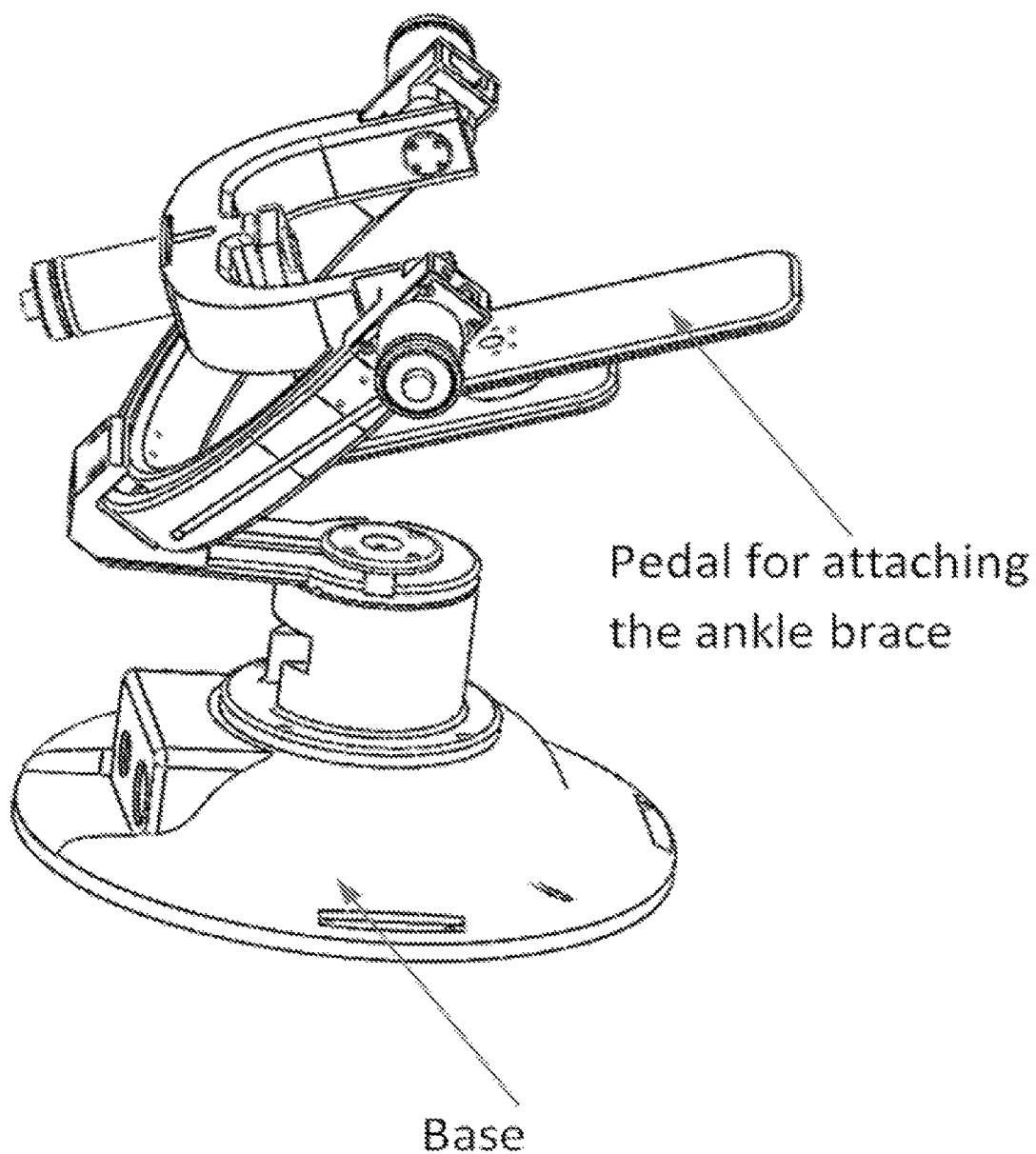
FIG. 6 is a perspective illustration of a robotic platform according to an exemplary embodiment of the present disclosure.
Figure 7:
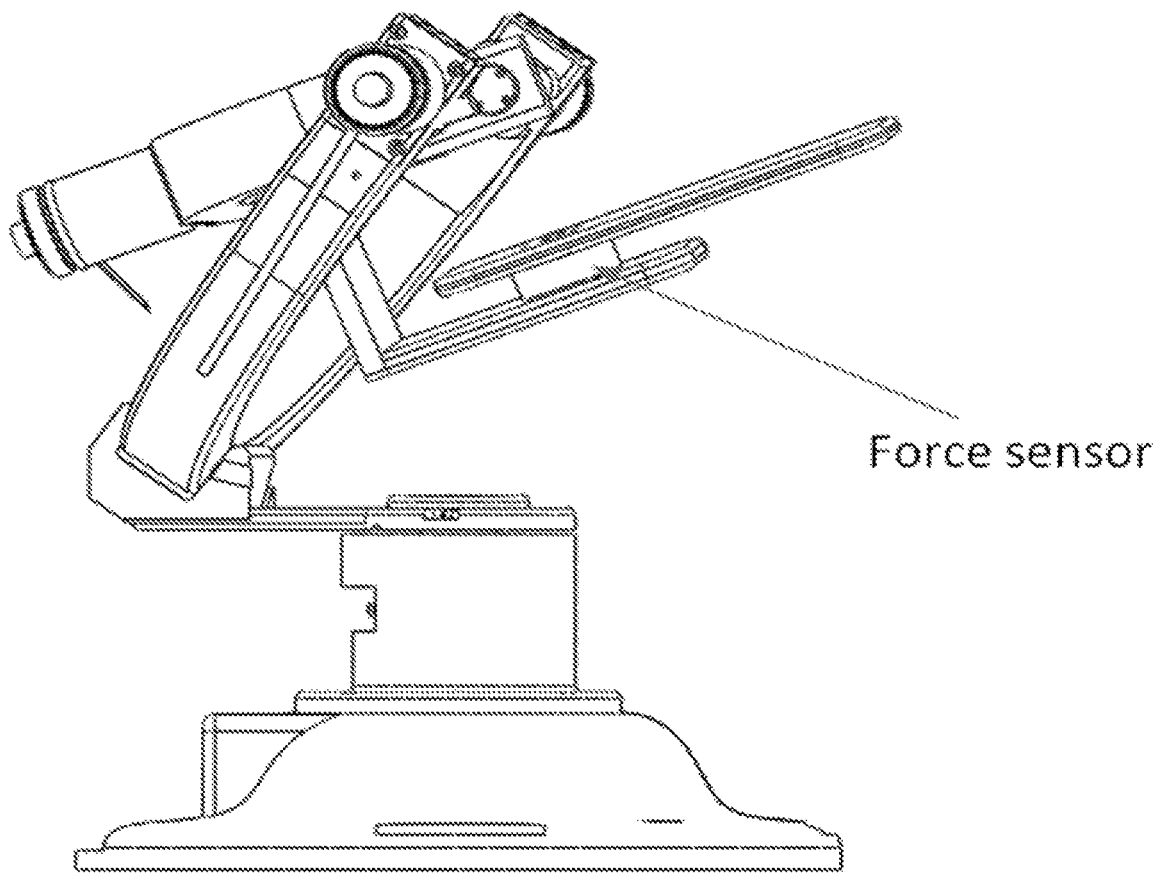
FIG. 7 is a front view of a robotic platform illustrating a force sensor according to an exemplary embodiment of the present disclosure.
Figure 8:
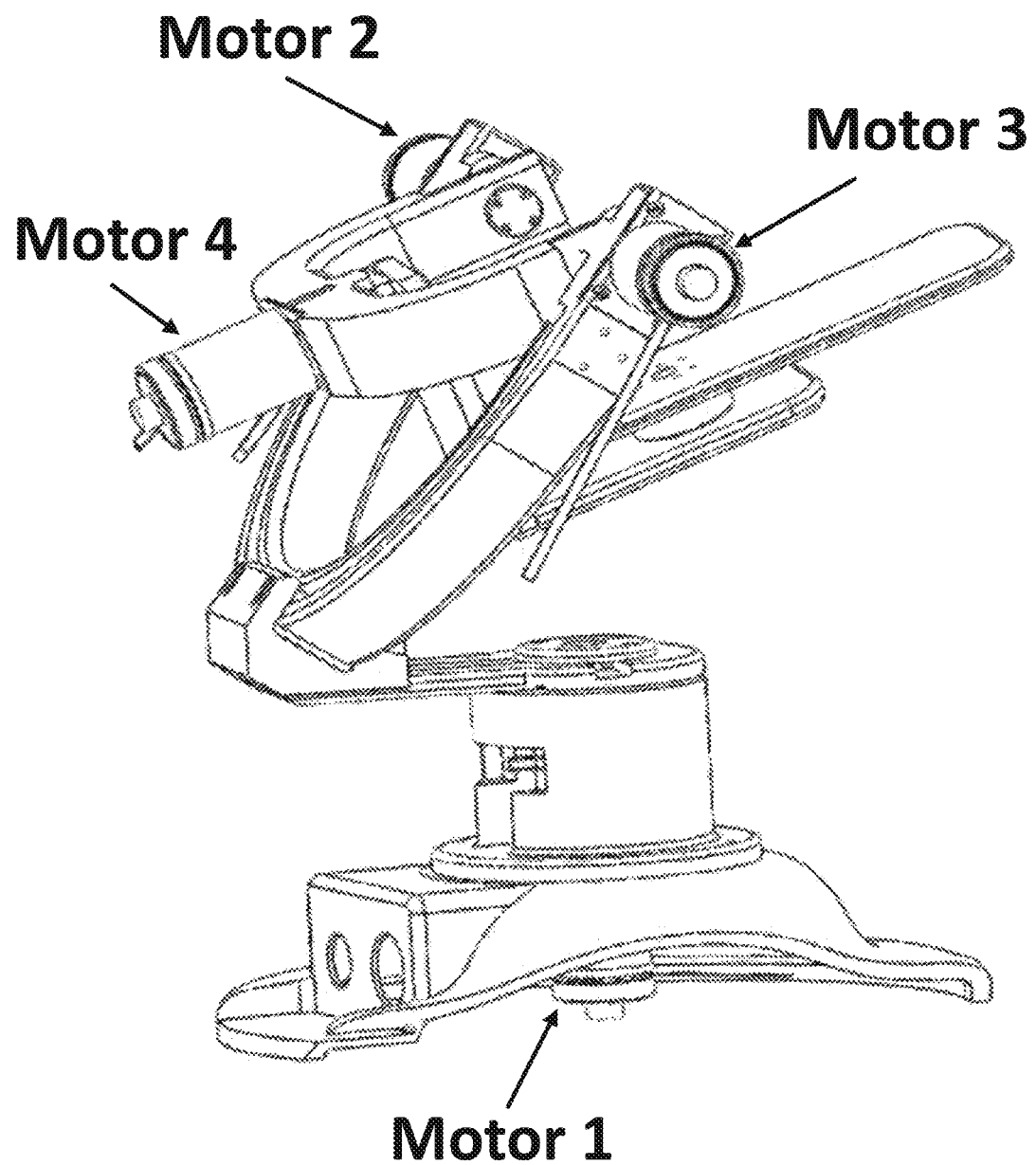
FIG. 8 is a perspective illustration of a robotic platform illustrating examples of locations of different motors according to an exemplary embodiment of the present disclosure.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

It is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Generally speaking, embodiments of the disclosed subject matter can involve a system, apparatus, and/or method for robotically assisted ankle rehabilitation, including a method of treatment, a method of providing the system or apparatus, and a method of using the system or apparatus. In one or more embodiments, the system, apparatus, or method can implement (or be implemented with) a video game system, whereby positioning and/or movement of the patient's ankle can be reflected in real time while the patient plays a video game as part of the patient's physical therapy.

Embodiments of the disclosed subject matter can find applications for various specific populations, such as children (pediatrics) and/or adults (e.g., geriatric), for ankle physical therapy or rehabilitation due to injury or a neuromuscular disorder, for instance, or simply for exercise, range of motion, or flexibility reasons.

FIGS. 1-8 illustrate a robotic platform according to exemplary embodiments of the present disclosure.

The robotic platform can include a motion platform and a motion controller. The motion platform can be a mechanical device having brackets connected to provide three degrees of freedom. Of course, in one or more embodiments, electronic components, such as one or more sensors and/or the motion controller can be part of the motion platform or coupled to the motion platform.

The motion platform can include a flat portion designed to receive and secure a user's foot. The motion platform can allow a user's leg to perform different motions such as a pitch (forward and backward leg movement), a yaw (rotation about a base of the motion platform), and a rotation or roll motion. The robotic platform can be used to perform each motion individually or a combination of motions that can be performed simultaneously. For example, pitch and yaw, or yaw and roll, or pitch, yaw and roll, or other possible combinations. In one or more embodiments, control may be based on a Remote Center of Motion (RCM) at or close to an ankle joint of the patient.

Limiting the robotic platform to three degrees of freedom can make the device lighter, compact and/or less expensive to manufacture. As such, the robotic platform becomes affordable for daily use and can be moved from one place to another including into a patients home.

The robotic platform can include a plurality of motors and corresponding gears sets (e.g., differential gear sets). For example, the robotic platform can include four motors such as MAXON's EC 4-pole brushless motors, and sensors such as an encoder, a motion sensor, a proximity sensor, an infrared sensor, and a force or a torque sensor. Notably, two of the motors can be provided on a pitch axis of the robotic platform. Further, such motors can be controlled in coordination with each other, based on signals received from the motion controller, for instance.

Safety features of the robotic platform can include one or more of mechanical stops in all joints, a maximum force limit, a maximum speed limit, and an emergency button to immediately stop the system.

The motion controller can control the motion platform by controlling one or more of the motors, for instance, to control resistance felt by a patient or to control movement of the motion platform (which may include preventing movement of the motion platform about a particular axis or axes). Such control may be based on position and/or movement sensors of the robotic platform that sense position and/or movement of the motion platform. Additionally or alternatively, such control may be based on one or more electromyography (EMG) signals from the patient.

Figure 9:
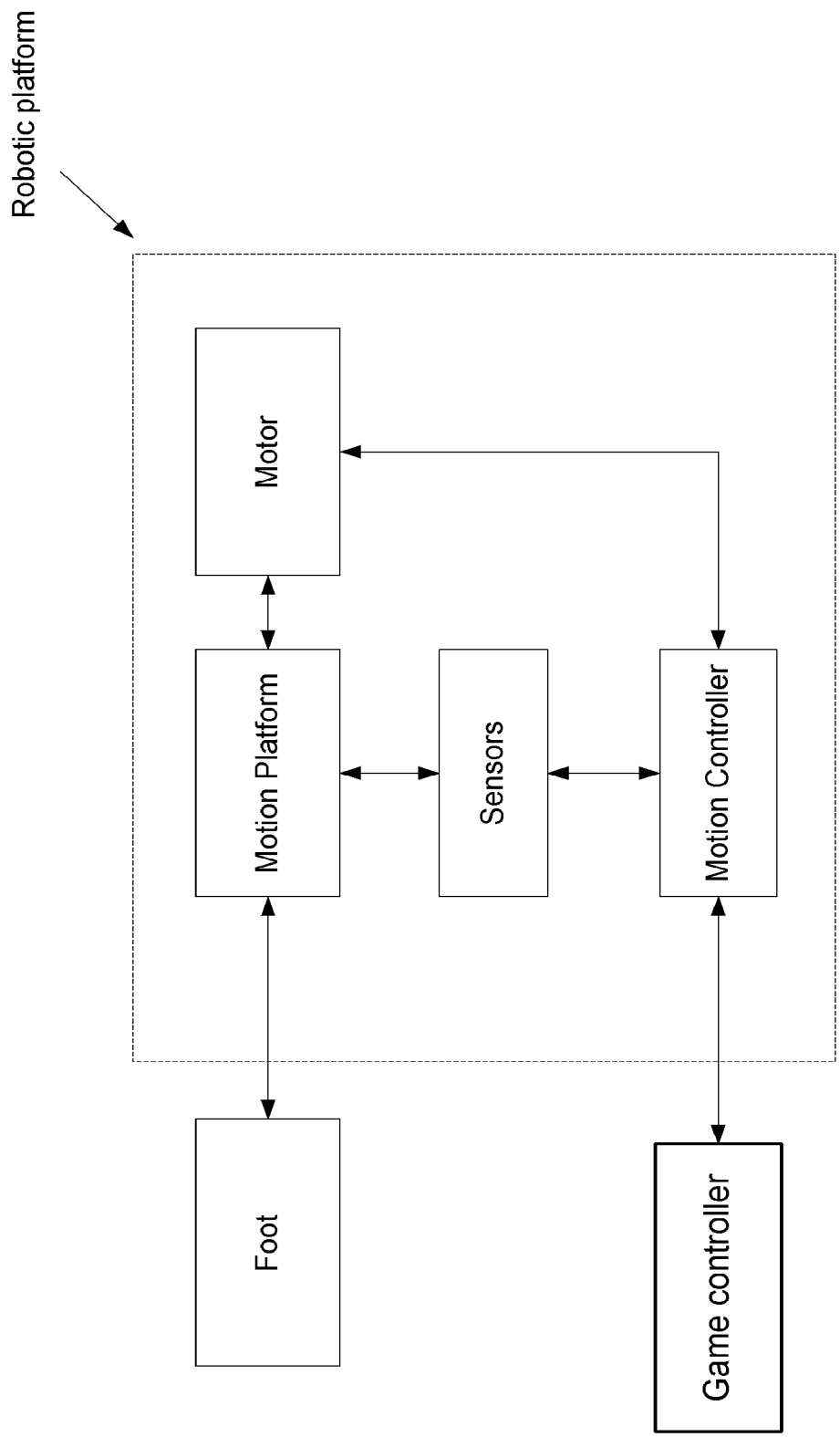
FIG. 9 is a block diagram of the robotic platform according to an exemplary embodiment of the present disclosure.

FIG. 9 is block diagram of the robotic platform according to an exemplary embodiment of the present disclosure. In FIG. 9, the robotic platform includes a motion platform, a plurality of motors, a plurality of sensors, and the motion controller. A user's foot can be placed and strapped on a pedal of the motion platform. The motion platform can be connected with a plurality of motors and sensors. The motion controller can control the plurality of motors to achieve a desired pitch, the yaw and the roll motion of the motion platform, or, alternatively, to prevent particular pitch, yaw, and/or roll motion. The motion controller can receive sensor data such as range of motion, force, torque, number of repetitions, etc. Based on the sensor data, the motion controller can control the rotation of the motors to achieve desired motion of the motion platform (which again may include no or limited motion of the platform).

The robotic platform can be operated in different modes such as: a passive mode and an active mode. A passive mode can mean, generally speaking, that the patient may be passive, and the robotic platform or a therapist controls the movement of the motion platform. Of course, in the passive mode the weight of the patient's foot and/or inadvertent resistance by the patient may also be taken into consideration when controlling movement of the motion platform, for instance. Generally speaking, the active mode can mean that the patient is intentionally causing the motion platform to move. Furthermore, active mode can be characterized as assistive or resistive, meaning that the robotic platform provides assistance or resistance, respectively, for instance, based on the patient's input. Implementing resistive mode by applying torque to the joint may be perceived as creating virtual springs in the selected joint to resist patient motion. Assistance mode can be implemented by adding additional torque, for instance, to help the patient reach a larger range of motion.

For example, the resistance can be adjusted based on the feedback of patient's performance, time of the day, etc. Further, the patient's performance can be categorized into low, medium and high. For low performance, the focus can be on building strength by high number of repetitions; for medium performance, the focus can be on increasing the resistance and for high performance the focus can be on both repetitions and resistance.

send signals wirelessly to a video game system (e.g., a controller for an XBOX® system) for integration of detected movement and/or positioning of the motion platform with the video game system. Thus, the patient can use the controller of the video game system to control movement of the motion platform based on the patient's response to the video game and, in turn, the robotic platform can send updated movement and/or position signals to the mobile wireless device.

In the game mode, the robotic platform is coupled to a video game such as FLIGHT SIMULATOR®, MARIO KART®, ANGRY BIRDS®, etc. The user can move the leg/foot to achieve a task defined in the video game. Further, the video game can include a point system, which can be used to determine the performance of the user's leg/foot. For example, if the user gathers more points for a pitch motion, then it can be indicative of good range and endurance. Similarly, if the user gathers more points for yaw motion, it can be indicative of the lateral leg strength. Also, if the user gathers more points for roll motion, it can be indicative of the flexibility of the ankle.

On the other hand, lack of points for particular motion (e.g., pitch, yaw, or roll) can be indicative of improvements required and the physical therapy can be adjusted accordingly. Furthermore, providing a game mode can motivate a child to do the physical therapy regularly at home, and have an enjoyable experience while doing so.

The game mode can be enabled by the motion controller. The motion controller can be configured to receive sensor data, analyze the motion, and transmit the motions to a video game controller. The motion controller can also perform several other functions. For example, the motion controller

| Factors | Repetitions | Pitch resistance | Yaw resistance | Roll resistance |
| --- | --- | --- | --- | --- |
| Morning | 20 for each motion | 10 units | 10 units | 10 units |
| Afternoon | 20 for each motion | 7 units | 7 units | 7 units |
| Evening | 20 for each motion | 3 units | 3 units | 3 units |
| 5 minutes before end of exercise | Just measure | 4 units | 2 units | 2 units |
| First 5 minutes of the exercise | Just measure | 2 units | 2 units | 2 units |
| Low | 75 for each motion | 1 units | 1 units | 1 units |
| Medium | 30 for each motion | 5 units for first 10 repetitions + increase by resistance 1 every 10 repetitions | 5 units for first 10 repetitions + increase by resistance 1 every 10 repetitions | 5 units for first 10 repetitions + increase by resistance 1 every 10 repetitions |
| High | 50 for each motion | 5 units for first 10 repetitions + increase by resistance 2 every 10 repetitions | 5 units for first 10 repetitions + increase by resistance 2 every 10 repetitions | 5 units for first 10 repetitions + increase by resistance 2 every 10 repetitions |

Figure 13:
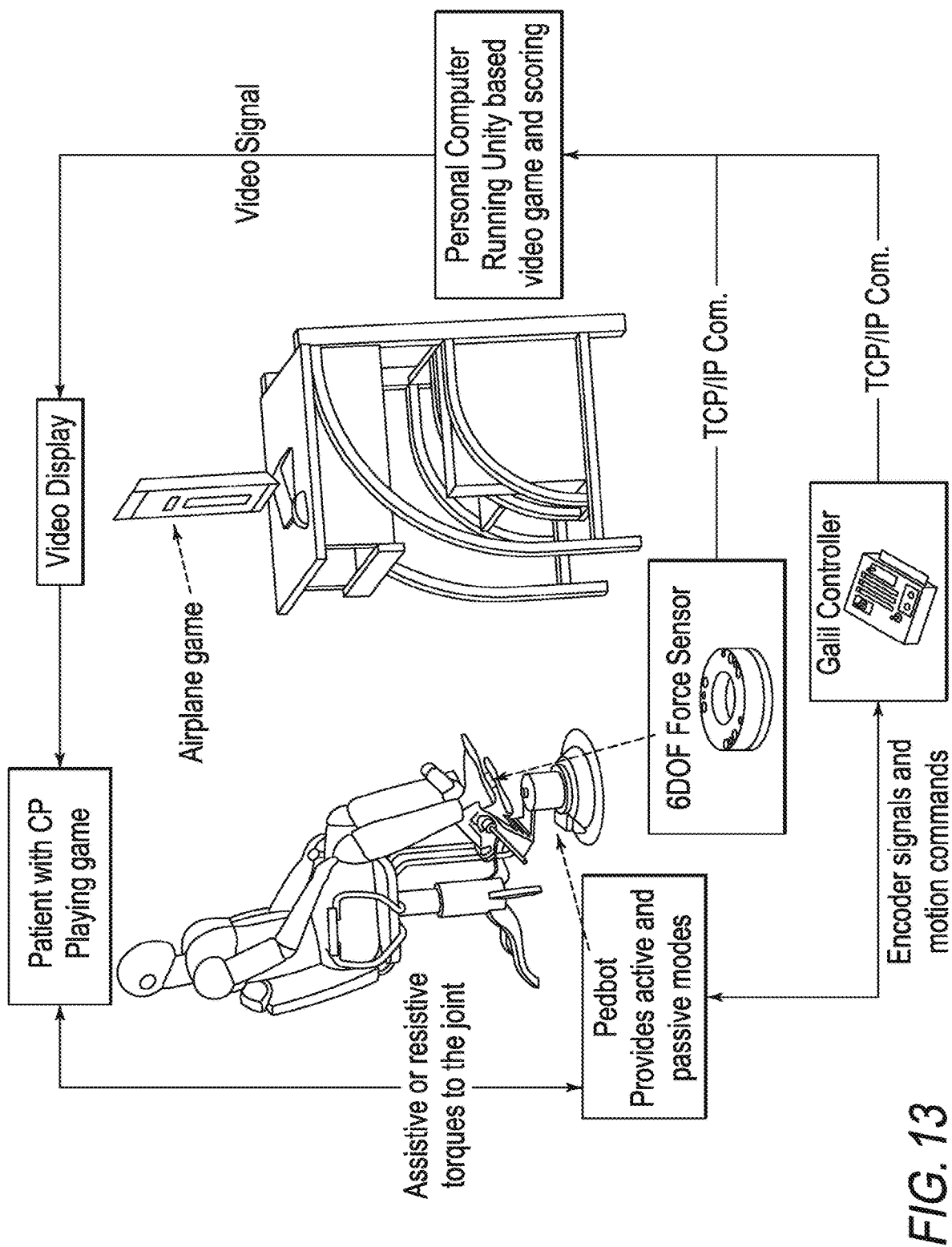
FIG. 13 is a block diagram of a system (or portions thereof) according to one or more embodiments of the present disclosure.
Figure 14:
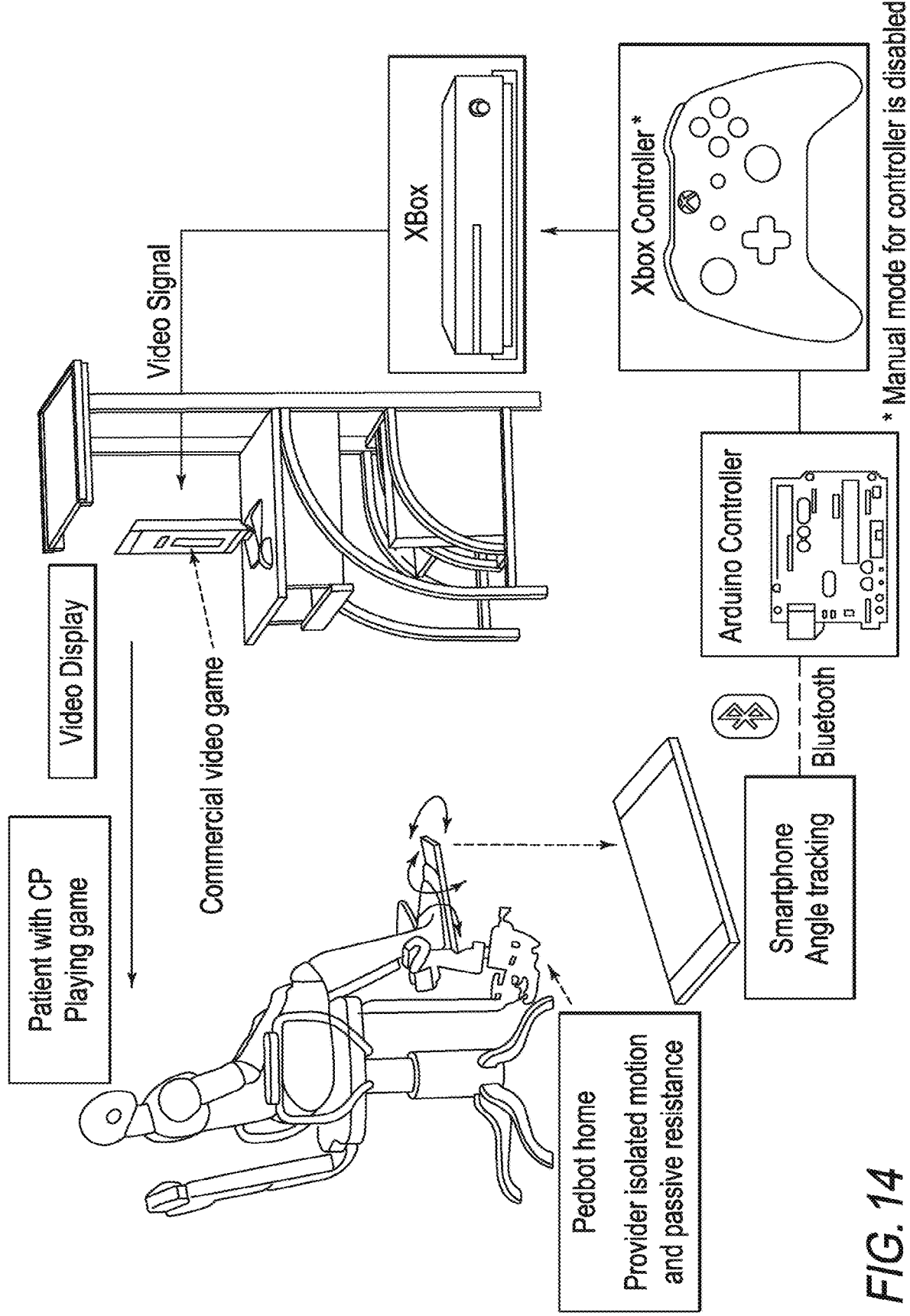
FIG. 14 is a block diagram of a system (or portions thereof) according to one or more embodiments of the present disclosure.

The robotic platform can also be operated in a game mode. FIG. 13 and FIG. 14 show non-limiting examples of systems, apparatuses, and methods according to various embodiments that implement a gaming mode. Generally, FIG. 13 shows a set up whereby signals from the robotic platform are processed by the motion controller and sent to a video game system (e.g., video game operating on a personal computer) via a wired communication interface, for instance, over a TCP/IP communication interface, whereas FIG. 14 shows a setup whereby signals from the motion controller are sent to a mobile wireless device (e.g., smartphone), which may track angles of the motion platform and can store the sensor data and monitor the progress of the user's leg/foot condition improvement. Further, based on the improvements or lack thereof, the motion controller can increase or decrease the range of motion, increase or decrease the number of repetitions of a particular motion, increase or decrease the resistance level, etc.

In one embodiment, two robotic platforms can be configured to communicate with each other and the motion controller of each robotic platform can provide an adoptive physical therapy based on the performance of each leg/foot. For example, a first robotic platform can be used for a left leg/foot and a second robotic platform can be used for a right leg/foot. The sensor data of the first robotic platform and the second robotic platform can be compared and analyzed to determine the number of repetitions for the left leg/foot vs. the right leg/foot, the resistance for the left leg/foot vs. the right leg/foot, type of motion for the left leg/foot vs. the right leg/foot, etc. For instance, the sensor data can indicate the left leg/foot can perform 100 repetitions of pitch movement in 10 minutes, while right leg/foot can perform 75 repetitions of pitch movement in 10 minutes. In this case, the resistance for the right leg/foot can be increased to strengthen the right leg/foot or the use of second robotic platform can continue for longer duration till 100 repetitions are completed while the left leg/foot rests and the time can be recorded. Furthermore, based on difference in time, the progress or improvement in leg/foot condition can be analyzed.

Furthermore, the motion controller can be configured to store particular motion patterns that are specifically designed for a patient. The motion patterns can be a set of exercises performed using the robotic platform in the presence of the therapist and recorded in a passive mode. The motion patterns can be activated based on a particular day, time, a threshold related to a range of motion or number of repetitions, etc. For example, a first motion pattern to be performed on a Monday at 10 am can be 50 pitch motions in 10 minutes, 10 yaw motions in 5 minutes, and 20 roll motions in 5 minutes. A second motion pattern to be performed on a Tuesday at 10 am can be 20 pitch motions in 5 minutes, 20 yaw motions in 10 minutes, and 40 roll motions in 10 minutes. In addition, in the game mode, a game can be designed to include tasks that follow the first motion pattern on Monday and the second motion pattern on Tuesday, thus making the physical therapy more interesting.

The motion controller can be further configured to detect a fatigue of the leg/foot, based on the range of motion and the speed of the motion, which can be observed especially towards the end of the exercise and activate a motor to further assist the user to complete an exercise routine.

In one embodiment, the robotic platform can be operated in a teletherapy mode, where the therapist can have a therapist robot, a copy of the robotic platform similar to that of the patient's robot, and the therapist robot can be used to remotely control the patient's robot while the patient is at home. For example, the therapist can perform the pitch motion, which can be transmitted, via a network to the patient's robotic platform. The motion controller of the patient's robotic platform can receive the pitch motion and the motion controller can further control the motor to move accordingly. Similarly, the yaw and the roll motion can also be transmitted.

Furthermore, one therapist can treat two or more patients simultaneously, where the patient's need to perform similar exercise routines.

Figure 10:
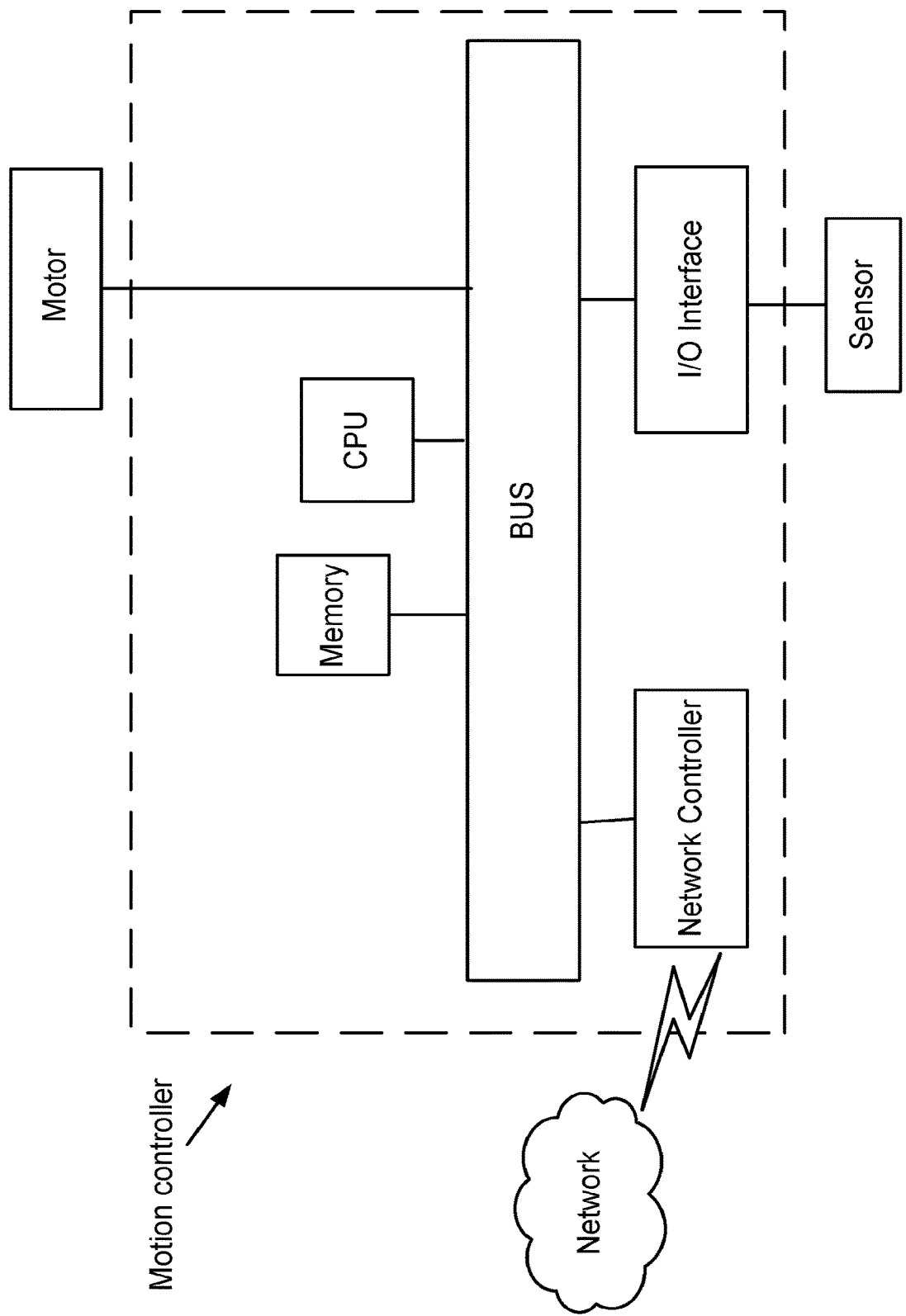
FIG. 10 is block diagram of a motion controller of a robotic platform according to an exemplary embodiment of the present disclosure.

FIG. 10 is block diagram of a motion controller of the robotic platform according to an exemplary embodiment of the present disclosure. In FIG. 10, the motion controller includes a Central Processing Unit (CPU) which performs the processes described in the present disclosure. The processed data and instructions may be stored in a memory. The hardware elements in order to achieve the motion controller may be realized by various circuitry elements, known to those skilled in the art. For example, CPU may be a Xenon or Core processor from Intel of America or an Opteron processor from AMD of America, ASIC processors or may be other processor types that would be recognized by one of ordinary skill in the art. Further, CPU may be implemented as multiple processors cooperatively working in parallel.

The motion controller, in FIG. 10, can also include a network controller for interfacing with a network. The motion controller can communicate with external devices such as a smart phone or a tablet, or other robotic platform via the network controller. As such, the performance of the patient can be monitored and analyzed remotely, and appropriate patient specific motion patterns can be designed. Furthermore, the motion controller can receive motion commands from external devices (e.g., of a doctor or a therapist) such as smart phone, tablets or servers via the network. An example user device is shown in FIG. 12, and an example server is shown in FIG. 11.

An Input/Output (I/O) interface can be used to connect with a variety of sensors such as a motion speed sensor, a pressure sensor, a force sensor, a torque sensor, an infrared sensor, etc. The sensor data can be transmitted to a remote server (shown in FIG. 11) via the network for analyzing the data or the analysis can be performed by the CPU of the motion controller. Furthermore, the motion controller can communicate with the motor via the bus.

Figure 11:
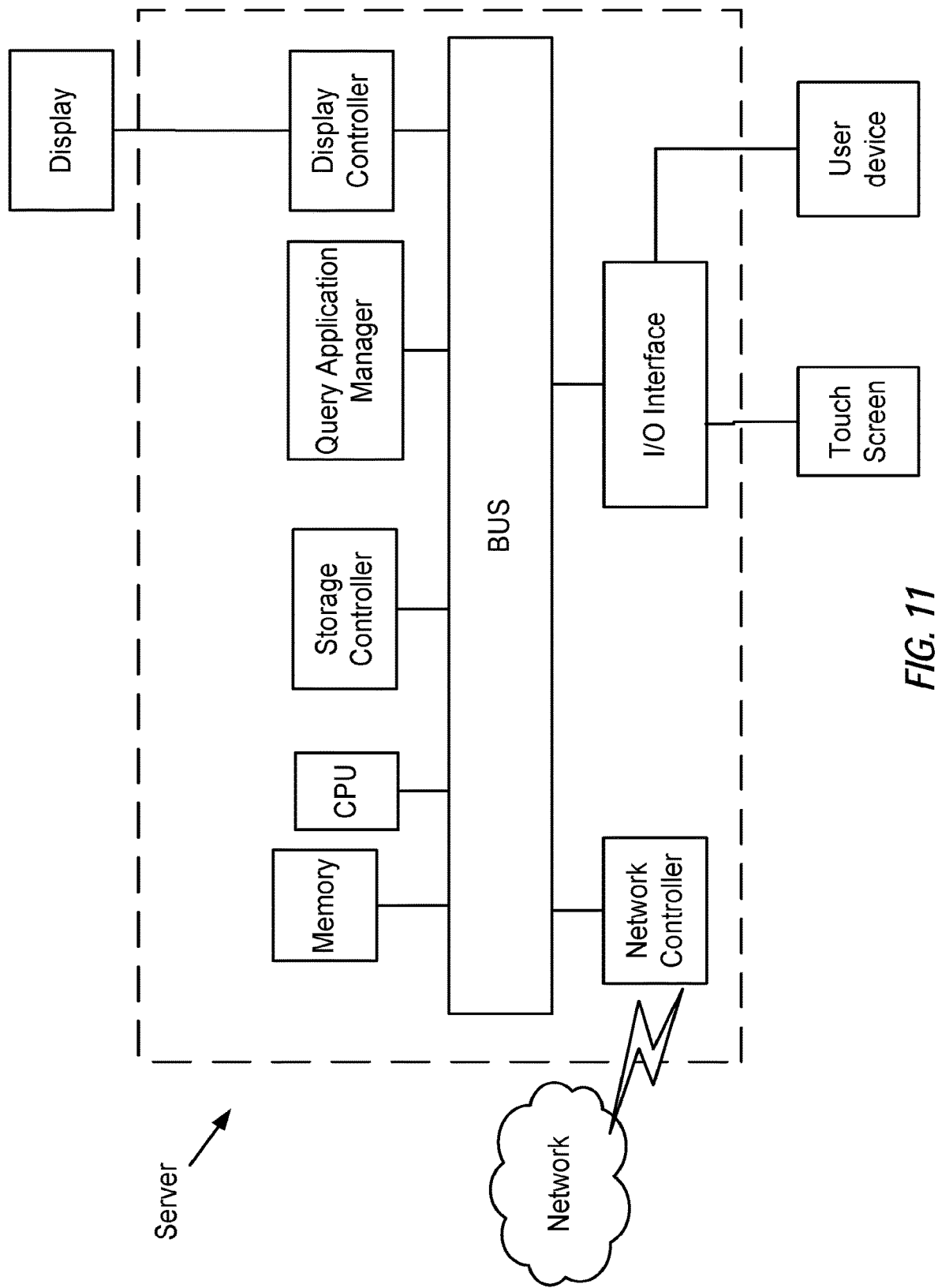
FIG. 11 is a block diagram of a server according to an exemplary embodiment of the present disclosure.
Figure 12:
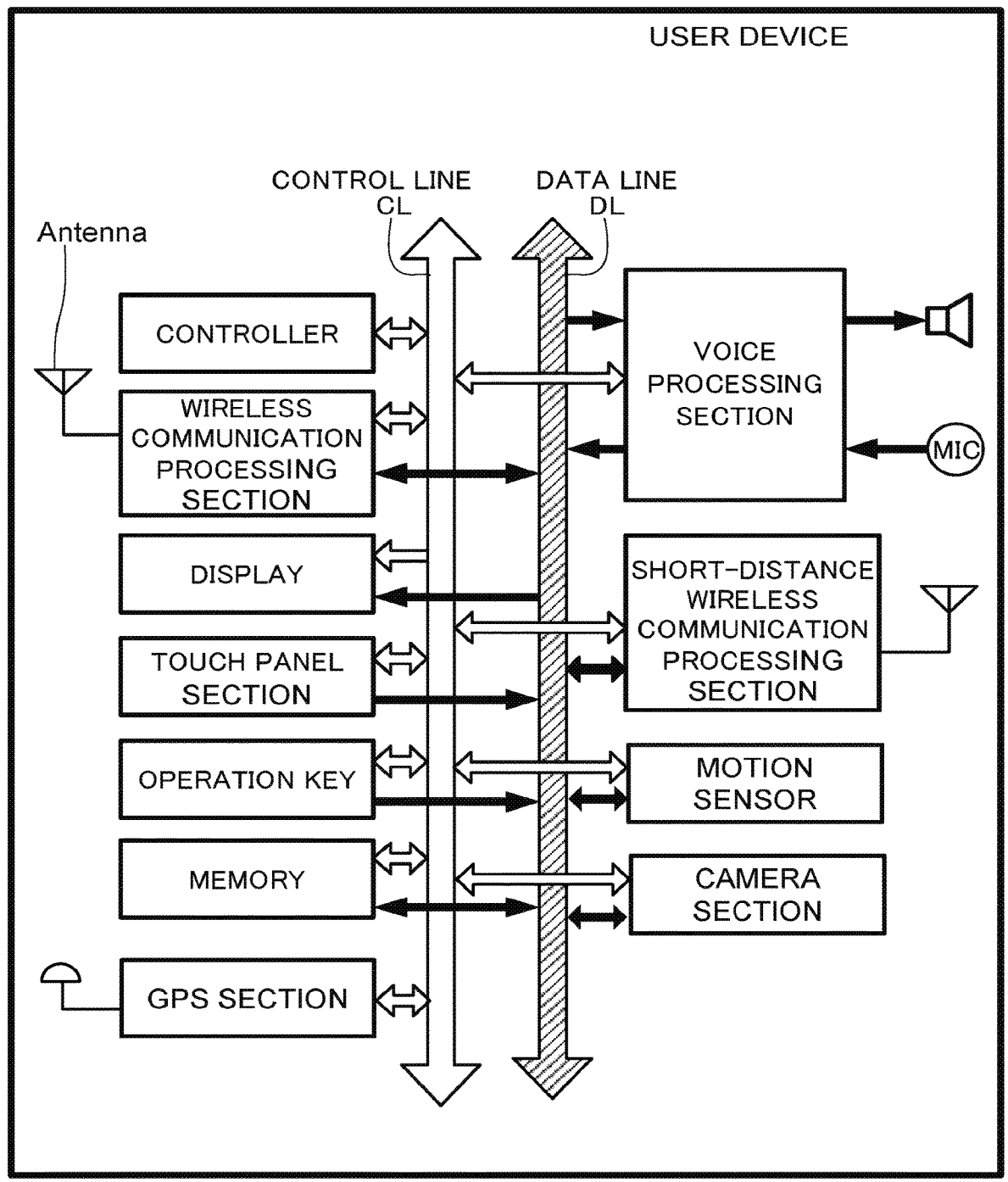
FIG. 12 is a block diagram of a user device according to an exemplary embodiment of the present disclosure.

In FIG. 11, the server includes a CPU which can be configured to receive inputs from the robotic platform and perform the processes described in the present disclosure. For example, the server can receive data from different patients and analyze the data in one central location. Further, the server can implement algorithms to determine the progress of a patient and send instructions to the motion controller of the particular patient to improve or adjust the performance. For example, instructions adjust the exercise routine, force or resistance of the robotic platform, etc. The process data and instructions may be stored in the memory.

Furthermore, the server can receive data from multiple robotic platform in real-time, analyze the performance of patient and adjust the motions, force, range of motion, or other performance metric based on the real-time data. The server can provide the feedback to the patient regarding the performance in real-time as well as after the exercise routine is completed. The server can display the performance of one or more patients in real-time via a display controller configured to display multiple patient data. Other function of the server can include, but not limited to, collecting and storing data for different patients, monitoring and recording the exercises for each patient, comparing data between different patients, determining if one patient is performing better than another patient, comparing different exercise routines of each patient, providing suggestions to change exercises routine based on comparison to improve performance of an under-performing patient, etc.

The hardware elements, in order to achieve the server, may be realized by various circuitry elements, known to those skilled in the art. For example, the CPU may be a XENON or Core processor from INTEL of America or an Opteron processor from AMID of America, or may be other processor types that would be recognized by one of ordinary skill in the art. Alternatively, the CPU may be implemented on an FPGA, ASIC, PLD or using discrete logic circuits, as one of ordinary skill in the art would recognize. Further, CPU may be implemented as multiple processors cooperatively working in parallel to perform the instructions.

The server can also include a network controller for interfacing with a network. Such network based interfacing can be useful to send commands from an external device such as a user device that is configured to communicate with the robotic controller. Thus, a user can send commands to the robotic platform remotely and operate the robotic platform in a teletherapy mode where the therapist can have a copy of the robot and be remotely controlling the patient's robot while the patient is at home.

As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi®, BLUETOOTH®, or any other wireless form of communication that is known.

The CPU of server can also perform functions related to communication control, audio signal processing, control for the audio signal processing, still and moving image processing and control, and other kinds of signal processing. The CPU may perform these functions by executing instructions stored in a memory.

The storage controller connects the memory with communication bus, which may be an ISA, EISA, VESA, PCI, or similar device, for interconnecting all of the components of the server. The query application manager processes the queries received from the user device or the motion controller. A description of the general features and functionality of the storage controller, network controller, the query manager and the I/O interface is omitted herein for brevity as these features are known.

FIG. 12 is a block diagram of the exemplary user device according to an embodiment of present disclosure. In certain embodiments, the user device may be remote wireless portable device, such as a smartphone. However, the skilled artisan will appreciate that the features described herein may be adapted to be implemented on other devices (e.g., a laptop, a tablet, a server, an e-reader, a camera, a navigation device, etc.). The exemplary user device includes a controller and a wireless communication processor connected to an antenna. Optionally, a speaker and a microphone are connected to a voice processor.

The controller may include one or more CPUs, and may control each element in the user device to perform functions related to communication control, audio signal processing, control for the audio signal processing, still and moving image processing and control, and other kinds of signal processing. The controller may perform these functions by executing instructions stored in a memory. Alternatively or in addition to the local storage of the memory, the functions may be executed using instructions stored on an external device accessed on a network or on a non-transitory computer readable medium.

The memory includes but is not limited to Read Only Memory (ROM), Random Access Memory (RAM), or a memory array including a combination of volatile and non-volatile memory units. The memory may be utilized as working memory by the controller while executing the processes and algorithms of the present disclosure. Additionally, the memory may be used for long-term storage, e.g., of image data and information related thereto. The memory may be configured to store the battle view information, operation view information and list of commands.

The user device can include a control line CL and data line DL as internal communication bus lines. Control data to/from the controller may be transmitted through the control line CL. The data line DL may be used for transmission of voice data, display data, etc.

The antenna can transmit/receive electromagnetic wave signals between base stations for performing radio-based communication, such as the various forms of cellular telephone communication. The wireless communication processor can control the communication performed between the user device and other external devices via the antenna. For example, the wireless communication processor may control communication between base stations for cellular phone communication.

The speaker can emit an audio signal corresponding to audio data supplied from the voice processor. The microphone can detect surrounding audio and converts the detected audio into an audio signal. The audio signal may then be output to the voice processor for further processing. The voice processor demodulates and/or decodes the audio data read from the memory or audio data received by the wireless communication processor and/or a short-distance wireless communication processor. Additionally, the voice processor may decode audio signals obtained by the microphone.

The exemplary user device may also include a display, a touch panel, an operation key, and a short-distance communication processor connected to an antenna. The display may be a Liquid Crystal Display (LCD), an organic electroluminescence display panel, or another display screen technology. In addition to displaying still and moving image data, the display may display operational inputs for control of the robotic platform. The display may additionally display a GUI for a user to control aspects of the user device and/or other devices such as the functions of the robotic platform. Further, the display may display characters and images received by the user device and/or stored in the memory or accessed from an external device on a network such as a camera. For example, the user device may access a network such as the Internet and display text and/or images transmitted from a Web server.

The touch panel may include a physical touch panel display screen and a touch panel driver. The touch panel may include one or more touch sensors for detecting an input operation on an operation surface of the touch panel display screen. The touch panel also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel may detect when the stylus approaches/contacts the operation surface of the touch panel display (similar to the case in which a finger is used for the touch operation).

In certain aspects of the present disclosure, the touch panel may be disposed adjacent to the display (e.g., laminated) or may be formed integrally with the display. For simplicity, the present disclosure assumes the touch panel is formed integrally with the display and therefore, examples discussed herein may describe touch operations being performed on the surface of the display rather than the touch panel. However, the skilled artisan will appreciate that this is not limiting.

For simplicity, the present disclosure assumes the touch panel is a capacitance-type touch panel technology. However, it should be appreciated that aspects of the present disclosure may easily be applied to other touch panel types (e.g., resistance-type touch panels) with alternate structures. In certain aspects of the present disclosure, the touch panel may include transparent electrode touch sensors arranged in the X-Y direction on the surface of transparent sensor glass.

The touch panel driver may be included in the touch panel for control processing related to the touch panel, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel may detect a position of a user's finger around an edge of the display panel (e.g., gripping a protective case that surrounds the display/touch panel). Signals may be transmitted by the touch panel driver, e.g. in response to a detection of a touch operation, in response to a query from another element based on timed data exchange, etc.

The touch panel and the display may be surrounded by a protective casing, which may also enclose the other elements included in the user device. In certain embodiments, a position of the user's fingers on the protective casing (but not directly on the surface of the display) may be detected by the touch panel sensors. Accordingly, the controller may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller may be configured to detect which hand is holding the user device, based on the detected finger position. For example, the touch panel sensors may detect a plurality of fingers on the left side of the user device (e.g., on an edge of the display or on the protective casing), and detect a single finger on the right side of the user device. In this exemplary scenario, the controller may determine that the user is wearing the user device with his/her right hand because the detected grip pattern corresponds to an expected pattern when the user device is wearing only with the right hand.

The operation key may include one or more buttons or similar external control elements, which may generate an operation signal based on a detected input by the user. In addition to outputs from the touch panel, these operation signals may be supplied to the controller for performing related processing and control. In certain aspects of the present disclosure, the processing and/or functions associated with external buttons and the like may be performed by the controller in response to an input operation on the touch panel display screen rather than the external button, key, etc. In this way, external buttons on the user device may be eliminated in lieu of performing inputs via touch operations, thereby improving water-tightness.

The antenna may transmit/receive electromagnetic wave signals to/from other external apparatuses, and the short-distance wireless communication processor may control the wireless communication performed between the other external apparatuses. Bluetooth®, IEEE 802.11, and near-field communication (NFC) are non-limiting examples of wireless communication protocols that may be used for inter-device communication via the short-distance wireless communication processor.

The user device may include a motion sensor. The motion sensor may detect features of motion (i.e., one or more movements) of the user device. For example, the motion sensor may include an accelerometer to detect acceleration, a gyroscope to detect angular velocity, a geomagnetic sensor to detect direction, a geo-location sensor to detect location, etc., or a combination thereof to detect motion of the user device. In certain embodiments, the motion sensor may generate a detection signal that includes data representing the detected motion. For example, the motion sensor may determine a number of distinct movements in a motion (e.g., from start of the series of movements to the stop, within a predetermined time interval, etc.), a number of physical shocks on the user device (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller, whereby further processing may be performed based on data included in the detection signal. The motion sensor can work in conjunction with a Global Positioning System (GPS) section. An antenna is connected to the GPS section for receiving and transmitting signals to and from a GPS satellite.

The user device may include a camera section, which includes a lens and shutter for capturing photographs of the surroundings around the user device. In an embodiment, the camera section captures surroundings of an opposite side of the user device from the user. The images of the captured photographs can be displayed on the display panel. A memory section saves the captured photographs. The memory section may reside within the camera section. The camera section can be a separate feature attached to the user device or it can be a built-in camera feature.

The motion controller, the server, and the user device (in FIG. 12) can be configured to perform functions specific to the robotic platform, and send and receive feedback specific to a patient's performance. When programmed to carry out function(s) described herein, the motion controller, the server, and the user device become special purpose devices.

Each of the functions of the described embodiments may be implemented by one or more processing circuits (circuitry). A processing circuit includes a programmed processor (for example, CPU discussed above), as a processor includes circuitry. A processing circuit may also include devices such as an application specific integrated circuit (ASIC) and conventional circuit components arranged to perform the recited functions.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art.

Embodiments of the disclosed subject matter may also be as set forth according to the parentheticals in the following paragraphs.

(1) A robotic platform system, comprising: a motion platform having three-degrees of freedom to achieve a pitch motion, a yaw motion and a roll motion; a plurality of motors connected to the motion platform to enable the pitch motion, the yaw motion and the roll motion of the motion platform; at least one sensor to collect data related to a motion including a range of motion, a number of repetitions, a speed, a force, or a torque; and a motion controller configured to receive the collected data from the at least one sensor, analyze the data to determine motion patterns, improvement over past performance and recommend new motion patterns to improve future performance, adjust a resistance level by adjusting the force or torque of at least one of the plurality of motors based on the analyzed data to customize motion patterns according to a performance feedback of a user, capture motions of the motion platform and transmit the motions to a game controller to achieve gaming tasks related to the motions, detect fatigue in a foot of the user based on the sensor data and provide power assistance to complete a motion, and control the movement of the plurality of motors.

(2) The system according to (1), wherein the motion patterns determination can be based on a day, a time of day, a beginning of an exercise routine, an end of an exercise routine, and a level of performance.

(3) The system according to (1) or (2), wherein the robotic platform is operated in a game mode, wherein the motions performed by the user are transformed into points earned.

(4) The system according to any one of (1) to (3), wherein the points earned are used to analyze the performance of the user and design exercise routines specific to the user.

(5) The system according to any one of (1) to (4), wherein the robotic platform is operated in a teletherapy mode, wherein the robotic platform is remotely controlled by a device controlled by a therapist.

(6) A method for operating a robotic platform, comprising: receiving data from at least one sensor of the robotic platform; analyzing the data to determine motion patterns, improvement over past performance and recommend new motion patterns to improve future performance; adjusting, via a network, a resistance level by adjusting a force or a torque of at least one of a plurality of motors of the robotic platform based on the analyzed data to customize motion patterns according to a performance feedback of a user; capturing motions of a motion platform of the robotic platform and transmitting the motions to a game controller to achieve gaming tasks related to the motions; detecting fatigue in a foot of the user based on the sensor data and providing a power assistance to complete a motion; and controlling the movement of the plurality of motors.

(7) A non-transitory computer-readable medium storing a program which when executed by a computer, causes the computer to perform a method for controlling a robotic platform, the method comprising: receiving data from at least one sensor of the robotic platform; analyzing the data to determine motion patterns, improvement over past performance and recommend new motion patterns to improve future performance; adjusting a resistance level by adjusting a force or a torque of at least one of a plurality of motors of the robotic platform based on the analyzed data to customize motion patterns according to a performance feedback of a user; and capturing motions of a motion platform of the robotic platform and transmitting the motions to a game controller to achieve gaming tasks related to the motions.

(8) A robotic platform system, comprising: a motion platform having three-degrees of freedom to achieve a pitch motion, a yaw motion and a roll motion; a plurality of motors connected to the motion platform to enable the pitch motion, the yaw motion and the roll motion of the motion platform; at least one sensor to collect data related to a motion including a range of motion, a number of repetitions, a speed, a force, or a torque; and a motion controller configured to receive the collected data from the at least one sensor, and analyze the data to determine motion patterns, improvement over past performance and recommend new motion patterns to improve future performance.

(9) The system according to (8), wherein the motion controller is configured to adjust a resistance level by adjusting the force or torque of at least one of the plurality of motors based on the analyzed data to customize motion patterns according to a performance feedback of a user.

(10) The system according to (8) or (9), wherein the motion controller is configured to capture motions of the motion platform and transmit the motions to a game controller to achieve gaming tasks related to the motions.

(11) The system according to any one of (8) to (10), wherein the motion controller is configured to detect fatigue in a foot of the user based on the sensor data and provide power assistance to complete a motion based on the detected fatigue.

(12) The system according to any one of (8) to (11), wherein the motion controller is configured to control movement of the plurality of motors based on the analyzed data.

(13) The system according to any one of (8) to (12), wherein the motion patterns determination is based on a day, a time of day, a beginning of an exercise routine, an end of an exercise routine, and a level of performance.

(14) The system according to any one of (8) to (13), wherein the robotic platform is operated in a game mode, wherein the motions performed by the user are transformed into points earned.

(15) The system according to any one of (8) to (14), wherein the points earned are used to analyze the performance of the user and design exercise routines specific to the user.

(16) The system according to any one of (8) to (15), wherein the robotic platform is operated in a teletherapy mode, wherein the robotic platform is remotely controlled by a device controlled by a therapist.

(17) The system according to any one of (8) to (16), wherein the plurality of motors include two motors on a pitch axis of the motion platform.

(18) The system according to any one of (8) to (17), wherein the motion controller is configured to control the plurality of motors based on a remote center of motion (RCM) defined by an intersection of roll, pitch, and yaw axes.

(19) The system according to any one of (8) to (18), wherein the motion controller is configured to control the plurality of motors based on one of a selectable assist mode and a selectable resist mode.

(20) The system according to any one of (8) to (19), wherein the motion controller is configured to receive one or more electromyography (EMG) signals and control the plurality of motors based on the received one or more EMG signals.

(21) The system according to any one of (8) to (20), wherein the motion controller is configured to output or provide data associated with the data collected from the at least one sensor to create a myelogram.

(22) The system according to any one of (8) to (21), wherein the motion controller is configured to output signals to integrate data concerning real time movement of the motion platform with a video game operating in real time.

(23) The system according to any one of (8) to (22), further comprising a portable wireless smart device configured to receive the output signals from the motion controller and send movement and/or position data to a processor of a video game system associated with the video game to implement the movement and/or positioning of the motion platform in the video game in real time.

(24) A method for operating a robotic platform, comprising: receiving data from at least one sensor of the robotic platform; and analyzing the data to determine motion patterns, improvement over past performance and recommend new motion patterns to improve future performance.

(25) The method of (24), further comprising: adjusting, via a network, a resistance level by adjusting a force or a torque of at least one of a plurality of motors of the robotic platform based on the analyzed data to customize motion patterns according to a performance feedback of a user; capturing motions of a motion platform of the robotic platform and transmitting the motions to a game controller to achieve gaming tasks related to the motions; detecting fatigue in a foot of the user based on the sensor data and providing a power assistance to complete a motion; and/or controlling the movement of the plurality of motors.

(26) A non-transitory computer-readable medium storing a program which when executed by a computer, causes the computer to perform a method for controlling a robotic platform, the method comprising: receiving data from at least one sensor of the robotic platform; and analyzing the data to determine motion patterns, improvement over past performance and recommend new motion patterns to improve future performance.

(27) The non-transitory computer-readable medium according to (26), wherein the method further comprises: adjusting a resistance level by adjusting a force or a torque of at least one of a plurality of motors of the robotic platform based on the analyzed data to customize motion patterns according to a performance feedback of a user; and/or capturing motions of a motion platform of the robotic platform and transmitting the motions to a game controller to achieve gaming tasks related to the motions.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures. For example, this technology may be structured for cloud computing whereby a single function is shared and processed in collaboration among a plurality of apparatuses via a network.

What is claimed is:

1. A robotic platform system for passive and active ankle rehabilitation, comprising:
a motion platform for receiving a user's foot and having three-degrees of freedom to achieve a pitch motion, a yaw motion and a roll motion;
a plurality of motors connected to the motion platform to enable the pitch motion, the yaw motion and the roll motion of the motion platform, the motors having an active mode and a passive mode, wherein the motors control movement of the platform in the passive mode and the motors provide supplemental assistance or resistance in the active mode;
at least one sensor to collect data related to a motion including a range of motion, a number of repetitions, a speed, a force, or a torque; and
a motion controller configured to
receive the collected data from the at least one sensor, and analyze the data to determine motion patterns pertaining to the user and the user's improvement over past performance and, based on the determined motion patterns and the improvement over past performance, recommend a customized motion pattern to improve the user's future performance.

2. The system according to claim 1, wherein the motion controller is configured to activate the customized motion pattern by being configured to adjust a resistance level by adjusting the force or torque of at least one of the plurality of motors based on the customized motion pattern.

3. The system according to claim 2, wherein the customized motion pattern includes an adjustment based on a threshold related to a range of motion or number of repetitions.

4. The system according to claim 1, wherein the motion controller is configured to capture motions of the motion platform and transmit the motions to a game controller to achieve gaming tasks related to the motions.

5. The system according to claim 1, wherein the motion controller is configured to detect fatigue in a foot of a user based on the sensor data and provide power assistance to complete a motion based on the detected fatigue.

6. The system according to claim 1, wherein the motion controller is configured to control movement of the plurality of motors based on the analyzed data.

7. The system according to claim 1, wherein the motion patterns determination is based on a day, a time of day, a beginning of an exercise routine, an end of an exercise routine, and a level of performance.

8. The system according to claim 1, wherein the robotic platform is operated in a game mode, wherein the motions performed by a user are transformed into points earned and are used to analyze the performance of the user and design exercise routines specific to the user.

9. The system according to claim 1, wherein the robotic platform is operated in a teletherapy mode, wherein the robotic platform is remotely controlled by a device controlled by a therapist.

10. The system according to claim 1, wherein the plurality of motors includes two motors on a pitch axis of the motion platform.

11. The system according to claim 1, wherein the motion controller is configured to control the plurality of motors based on a remote center of motion (RCM) defined by an intersection of roll, pitch, and yaw axes.

12. The system according to claim 1, wherein the motion controller is configured to control the plurality of motors based on one of a selectable assist mode and a selectable resist mode.

13. The system according to claim 1, wherein the motion controller is configured to receive one or more electromyography (EMG) signals and control the plurality of motors based on the received one or more EMG signals.

14. The system according to claim 1, wherein the motion controller is configured to output or provide data associated with the data collected from the at least one sensor to create a myelogram.

15. The system according to claim 1, wherein the motion controller is configured to output signals to integrate data concerning real time movement of the motion platform with a video game operating in real time.

16. The system according to claim 15, further comprising a portable wireless smart device configured to receive the output signals from the motion controller and send movement and/or position data to a processor of a video game system associated with the video game to implement the movement and/or positioning of the motion platform in the video game in real time.

17. A method for operating a robotic platform, comprising:
 providing robotic platform system for passive and active ankle rehabilitation, including:
  a motion platform for receiving a user's foot and having three-degrees of freedom to achieve a pitch motion, a yaw motion and a roll motion,
  a plurality of motors connected to the motion platform to enable the pitch motion, the yaw motion and the roll motion of the motion platform, the motors having an active mode and a passive mode, wherein the motors control movement of the platform in the passive mode and the motors provide supplemental assistance or resistance in the active mode,
  at least one sensor to collect data related to a motion including a range of motion, a number of repetitions, a speed, a force, or a torque, and
  a motion controller;
 receiving, using the motion controller, data from at least one sensor of the robotic platform; and
 analyzing, using the motion controller, the data to determine motion patterns pertaining to the user and the user's improvement over past performance and, based on the determined motion patterns and the improvement over past performance, recommend a customized motion pattern to improve the user's future performance.

18. The method of claim 17, further comprising:
 adjusting, via a network, a resistance level by adjusting a force or a torque of at least one of a plurality of motors of the robotic platform based on the analyzed data to customize motion patterns according to a performance feedback of a user;
 capturing motions of a motion platform of the robotic platform and transmitting the motions to a game controller to achieve gaming tasks related to the motions;
 detecting fatigue in a foot of the user based on sensor data and providing a power assistance to complete a motion; and
 controlling movement of the plurality of motors.

\* \* \* \* \*